(12) United States Patent
Yueh

(10) Patent No.: US 11,213,716 B2
(45) Date of Patent: Jan. 4, 2022

(54) MUSCLE TRAINING APPARATUS CAPABLE OF GENERATING FORCE

(71) Applicants: Oivita Creative Co., Ltd., Taipei (TW); Chao-Yu Yueh, Taipei (TW)

(72) Inventor: Chao-Yu Yueh, Taipei (TW)

(73) Assignees: OIVITA CREATIVE CO., LTD., Taipei (TW); Chao-Yu Yueh, Taipei (TW)

(*) Notice: Subject to any disclaimer, the term of this patent is extended or adjusted under 35 U.S.C. 154(b) by 199 days.

(21) Appl. No.: 16/578,533

(22) Filed: Sep. 23, 2019

(65) Prior Publication Data
US 2020/0101345 A1 Apr. 2, 2020

(30) Foreign Application Priority Data
Sep. 28, 2018 (TW) ................. 107134285

(51) Int. Cl.
| | |
|---|---|
| A63B 21/22 | (2006.01) |
| A63B 21/005 | (2006.01) |
| A63B 23/20 | (2006.01) |
| A63B 43/00 | (2006.01) |

(52) U.S. Cl.
CPC ........ *A63B 21/222* (2015.10); *A63B 21/0058* (2013.01); *A63B 23/20* (2013.01); *A63B 43/004* (2013.01); *A63B 2209/00* (2013.01); *A63B 2220/56* (2013.01); *A63B 2220/833* (2013.01); *A63B 2225/50* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,645,203 B2 * | 1/2010 | Tang | ............ | A63B 41/085 473/604 |
| 8,628,453 B2 * | 1/2014 | Balakrishnan | ..... | A63B 24/0021 482/1 |
| 9,257,054 B2 * | 2/2016 | Coza | ............ | A63B 43/004 |
| 9,504,414 B2 * | 11/2016 | Coza | ............ | G06F 3/011 |
| 10,675,512 B2 * | 6/2020 | Corbeil | ............ | A63B 43/004 |
| 10,775,941 B2 * | 9/2020 | Heath | ............ | A63B 43/004 |
| 2005/0107227 A1 * | 5/2005 | Massey | ............ | A63B 21/04 482/121 |
| 2005/0143234 A1 * | 6/2005 | Massey | ............ | A63B 21/04 482/140 |
| 2005/0277499 A1 * | 12/2005 | Tang | ............ | A63B 41/085 473/604 |
| 2009/0048044 A1 * | 2/2009 | Oleson | ............ | A63B 43/00 473/570 |

(Continued)

*Primary Examiner* — Garrett K Atkinson
(74) *Attorney, Agent, or Firm* — McClure, Qualey & Rodack, LLP

(57) ABSTRACT

A muscle training apparatus capable of generating a force is disclosed. The muscle training apparatus includes a second support shell, a force-generating unit and an elastic covering unit. The second support shell is spherical and has a second containing space. The force-generating unit is disposed and fixed in the second containing space of the second supporting shell for generating a force. The elastic covering unit covers the second support shell to have a soft surface. The muscle training device can generate a force in a specific direction and intensity by the force-generating unit.

11 Claims, 7 Drawing Sheets

(56) References Cited

U.S. PATENT DOCUMENTS

| | | | |
|---|---|---|---|
| 2010/0184563 A1* | 7/2010 | Molyneux | A63B 24/0021 482/1 |
| 2011/0304497 A1* | 12/2011 | Molyneux | A63B 24/0021 342/42 |
| 2013/0130843 A1* | 5/2013 | Burroughs | A43B 5/02 473/415 |
| 2015/0328516 A1* | 11/2015 | Coza | G09B 19/0038 473/446 |
| 2017/0304685 A1* | 10/2017 | Iqbal | B32B 5/022 |
| 2018/0117436 A1* | 5/2018 | Coza | G09B 19/0038 |
| 2018/0188850 A1* | 7/2018 | Heath | A63B 71/0622 |
| 2018/0214755 A1* | 8/2018 | Villalba | A63J 7/00 |
| 2019/0091520 A1* | 3/2019 | Corbeil | A63B 41/08 |
| 2019/0184241 A1* | 6/2019 | Hut | A63B 41/02 |
| 2021/0077862 A1* | 3/2021 | Hutt | A63B 41/02 |

\* cited by examiner

MUSCLE TRAINING APPARATUS CAPABLE OF GENERATING FORCE

CROSS REFERENCE TO RELATED APPLICATIONS

This Non-provisional application claims priority under 35 U.S.C. § 119(a) on Patent Application No. 107134285 filed in Taiwan on Sep. 28, 2018, the entire contents of which are hereby incorporated by reference.

BACKGROUND

1. Technical Field

The invention relates to a training apparatus, in particular, to a muscle training apparatus capable of generating force.

2. Description of Related Art

Kegel exercise is a prescription-specified exercise for pregnant women. Its main purpose is to increase muscle tension by stretching the pubococcygeus of the pelvic floor, so as to make the pelvic floor be ready for the physiological stress caused by late pregnancy and childbirth.

The so-called Kegel ball was also developed by some practitioners to train the pubococcygeus through placing steel balls inside it, so as to achieve the effect of Kegel exercise by use the Kegel ball only, or strengthen the training effect by matching with the Kegel exercise.

The above-mentioned conventional Kegel ball has at least the following shortcomings: first, after doing Kegel exercise or training with Kegel balls, users or even doctors usually cannot know the state of muscles and it is difficult to judge the results of the training; second, the familiar Kegel ball only uses the steel balls inside it to increase the bear load, however, the steel balls moves freely and as a result the training effect cannot be controlled.

Therefore, it is one of the important subject matter to develop a muscle training apparatus that can generate controllable force and have the muscle strength testing function, so as to solve the problems above.

SUMMARY OF THE INVENTION

In view of the foregoing, the invention is to provide a muscle training apparatus capable of generating a controllable force to train the specific muscle groups.

To achieve the above, a muscle training apparatus capable of generating a force includes a second support shell, a force-generating unit and an elastic covering unit. The second support shell is spherical and has a second containing space. The force-generating unit is arranged and fixed in the second containing space to generate a force. The elastic covering unit covers the second support shell to make it have a soft surface. By means of the force-generating unit, the muscle training apparatus can generate a force in specific direction and intensity.

In one embodiment of the invention, wherein the elastic covering unit is an integrally formed silica gel.

In one embodiment of the invention, wherein the force-generating unit includes a gyroscope and a motor. The gyroscope has a rotor and generates force through the rotation of the rotor; and the motor is connected with the rotor to drive it.

In one embodiment of the invention, the muscle training apparatus further includes a steering mechanism, which is arranged in the second containing space and is connected between the force-generating unit and the second support shell. The steering mechanism makes the force-generating unit move relative to the second support shell. In other embodiments, the steering mechanism may be connected between the gyroscope and the second support shell to enable the gyroscope to move relative to the second support shell.

In one embodiment of the invention, wherein the steering mechanism has a first fixing part, a second fixing part and a pivot. The first fixing part is connected to the second support shell; the second fixing part is connected to the force-generating unit or the gyroscope, and the pivot is connected between the first fixing part and the second fixing part.

In one embodiment of the invention, the muscle training apparatus further includes a first support shell, a plurality of membrane pressure-sensing units, an arithmetic processing unit and a signal transmission unit. The first support shell is spherical and has a first outer surface and a first containing space; the membrane pressure-sensing units are respectively arranged on the first outer surface of the first support shell; the arithmetic processing unit is arranged in the first containing space of the first support shell and is electrically connected with the membrane pressure-sensing units respectively; and the signal transmission unit is arranged in the first containing space of the first support shell and electrically connected with the arithmetic processing unit.

In one embodiment of the invention, wherein the first support shell has a first end and a second end, which are arranged opposite to each other. The first end is divided into four quadrants according to an axis, each quadrant is provided with at least one membrane pressure-sensing unit.

In one embodiment of the invention, the muscle training apparatus further includes a power supply unit, which is arranged in the first containing space of the first support shell or in the second containing space of the second support shell to output a power supply.

In one embodiment of the invention, the muscle training apparatus further includes a circuit board, which is arranged in the first containing space of the first support shell. The arithmetic processing unit, signal transmission unit or power supply unit are disposed and electrically connected to the circuit board.

In one embodiment of the invention, wherein the signal transmission unit is a wireless signal transmission unit.

In one embodiment of the invention, wherein one inner surface of the elastic covering unit is in contact with such membrane pressure-sensing units.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Reference will now be made to the drawings to describe various inventive embodiments of the present disclosure in detail, wherein like numerals refer to like elements throughout.

Figure 1:
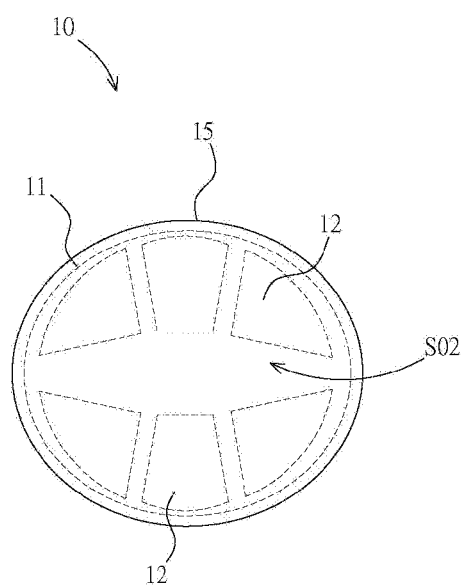
FIG. 1 is a schematic diagram showing the configuration of a muscle training apparatus according to the first embodiment of the invention.
Figure 2:
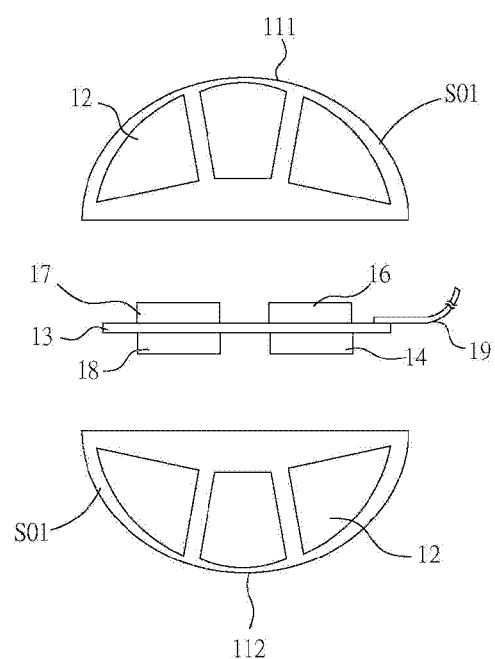
FIG. 2 is an explosion diagram showing a part of the muscle training apparatus.

Please refer to FIGS. 1 and 2 to illustrate the muscle training apparatus according to the first embodiment of the invention. As shown in FIGS. 1 and 2, the muscle training apparatus 10 includes a first support shell 11, a plurality of membrane pressure-sensing units 12, a circuit board 13, an arithmetic processing unit 14 and an elastic covering unit 15.

The first support shell 11 has a first outer surface S01 and a first containing space S02. In the embodiment, the first support shell 11 is elliptical spherical or egg-shaped, and has a first sub-shell 111 and a second sub-shell 112, which can be joined together to form the first support shell 11 with the first containing space S02. The first support shell 11 may be made of materials with sufficient hardness and supporting capacity like resin, polymer, ceramic or metal, etc.

The membrane pressure-sensing units 12 are arranged on the first outer surface S01 of the first support shell 11. Due to their flexibleness, the membrane pressure-sensing units 12 can fit to the outer surface S01 of the first support shell 11. In the embodiment, the outer surface S01 of the first support shell 11 has a plurality of setting areas (not shown in the figure), the number of which corresponds to the number of the membrane pressure-sensing units 12. The membrane pressure-sensing units 12 can be fixed in the corresponding setting area with bonding glue.

Although the overall shape of the first support shell 11 is spherical, the setting area can be designed as planar so that the membrane pressure-sensing units 12 can fit to it well and be fixed easily.

The first support shell 11 may also have at least one opening to connect the first containing space S02 with its outside. The connecting wire of the membrane pressure-sensing units 12 can enter the first containing space S02 through this opening.

The circuit board 13 is arranged in the first containing space S02 and fixed on the first support shell 11. The substrates of circuit board 13 can be selected from ceramic, glass, resin or metal.

The arithmetic processing unit 14 is arranged on the circuit board 13 and electrically connected with the membrane pressure-sensing units 12, so as to receive the signal output from the membrane pressure-sensing units 12 for judging the strength of external pressure.

The elastic covering unit 15 is made of integrally formed silica gel and covers the first support shell 11.

Figure 3:
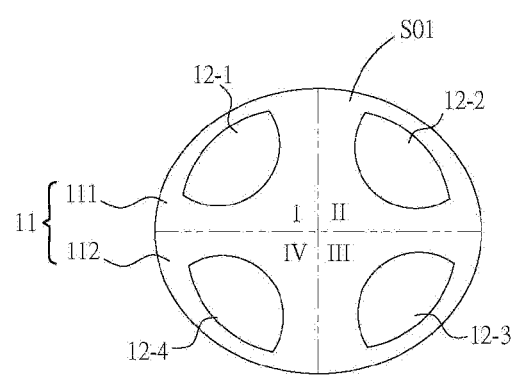
FIG. 3 is a side view of the muscle training apparatus.

The first support shell 11 is elliptical, and it has opposite a first end and a second end along the long axis of the ellipse. Referring to FIG. 3, there are four quadrants I-IV according to the long axis of the ellipse as seen from the first end of the first support shell 11, and each quadrant is provided with a membrane pressure-sensing unit. In the embodiment, for example, the membrane pressure-sensing unit 12-1 is set in quadrant I, the membrane pressure-sensing unit 12-2 is set in quadrant II, the membrane pressure-sensing unit 12-3 is set in quadrant III, and the membrane pressure-sensing unit 12-4 is set in quadrant IV. Full quadrant data can be obtained with the membrane pressure-sensing units 12-1 to 12-4 in four quadrants.

From above, the first end of the first support shell 11 will first contact with the muscle during the muscle training apparatus 10 enters the pubococcygeus, so the membrane pressure-sensing units 12-1 to 12-4 set at the first end will detect the pressure at this time, through which the strength of the muscle can be known and the quantitative data of muscle strength can be obtained.

Furthermore, the second end of the first support shell 11 could also be configured similar to that of the first end to have four membrane pressure-sensing units 12. And, between the first end and the second end, it is the area with largest circumference of the first support shell 11, where four membrane pressure-sensing units 12 can be set around. As mentioned above, by setting 12 membrane pressure-sensing units 12 on the first support shell 11, the omnidirectional muscle strength can be detected.

Figure 4:
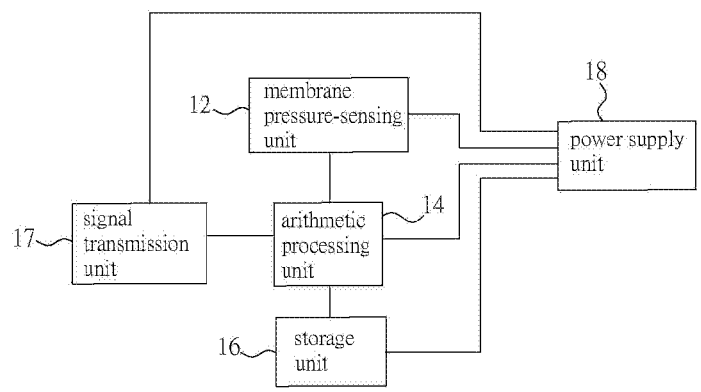
FIG. 4 is a block diagram showing the circuit configuration of the muscle training apparatus.

Next, please also refer to FIGS. 2 and 4, FIG. 4 shows the circuit block diagram of the muscle training apparatus 10, which includes also a storage unit 16, a signal transmission unit 17, a power supply unit 18 and a flexible circuit board 19.

The flexible circuit board 19 is electrically connected between the membrane pressure-sensing units 12 and the circuit board 13 so as to transmit the signals detected by the membrane pressure-sensing units 12.

The arithmetic processing unit 14 is electrically connected with the membrane pressure-sensing units 12, the storage unit 16 and the signal transmission unit 17, respectively. The arithmetic processing unit 14 is, for example, a microprocessor or a central processing unit (CPU), or other components with arithmetic processing capability to process information detected by the membrane pressure-sensing units 12, that is to convert the data format of the information detected by the membrane pressure-sensing units 12, which could also be integrated with other health or environmental information.

The storage unit 16 can store the information output by the arithmetic processing unit 14, which is to store the health and environmental information corresponding to the muscle strength testing. The storage unit 16, for example, is a flash memory, or other volatile memory or non-volatile memory, which is not restricted here.

The signal transmission unit 17 can be either a wired or a wireless one, which can transfer the information stored in the storage unit 16 to other electronic devices or receive information from outside. The wired signal transmission unit is, for example, USB, while the wireless one is, for example, Bluetooth or Wi-Fi. The signal transmission unit 17 can transmit information such as test results to Cloud storage space, or mobile communication devices or computers installed with corresponding application programs.

The power supply unit 18 is electrically connected to the membrane pressure-sensing units 12, the arithmetic processing unit 14, the storage unit 16 and the signal transmission unit 17, respectively; and provides power to each unit for their operation.

Therefore, the muscle training apparatus of the invention is arranged with a plurality of membrane pressure-sensing units based on the concept of zoning detection to detect different zones independently, so as to obtain comprehensive testing data that is helpful to judge the results of muscle training. In addition, the test results can be transmitted to the corresponding electronic devices in real time for users to interpret and then improve the practicability.

Figure 5:
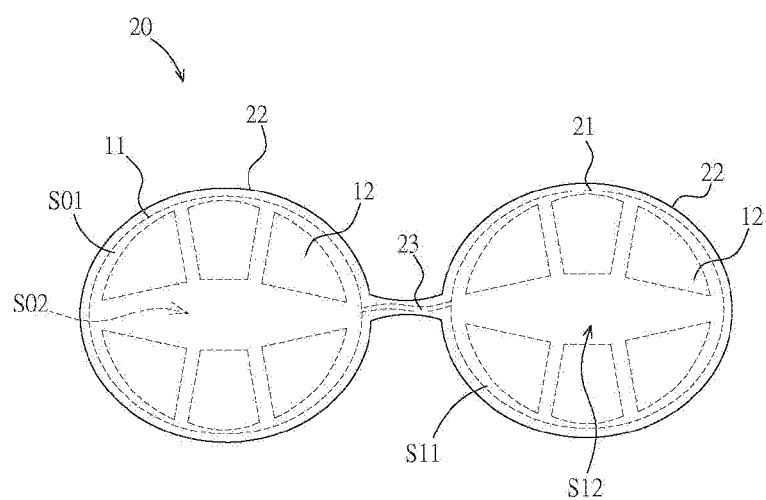
FIG. 5 is a schematic diagram showing the configuration of a muscle training apparatus according to the second embodiment of the invention.

Next, please refer to FIG. 5 to illustrate the muscle training apparatus according to the second embodiment of the invention. As shown in FIG. 5, the difference between the muscle training apparatus 20 and the muscle training apparatus 10 of the abovementioned first embodiment is that the former includes a second support shell 21, which is adjacent to the first support shell 11 and is covered in an elastic covering unit 22 together with the first support shell.

Being similar to the first support shell 11, the second support shell 21 is also elliptical spherical and has a second outer surface S11 and a second containing space S12. The membrane pressure-sensing units 12 are arranged on the second outer surface S11 of the second support shell 21 for muscle strength testing. Please also refer to aforesaid FIG. 2, the membrane pressure-sensing units 12 set on the second outer surface S11 can be electrically connected with the arithmetic processing unit 14 in the first support shell 11 through a flexible circuit board 23. The flexible circuit board 23 can be wired first into the second containing space S12 from the second outer surface S11 and pass through the second support shell 21, finally enter the first containing space S02 of the first support shell 11 and then is electrically connected to the circuit board 13. However, in other embodiments, the wiring mode is not limited to this, and any way of electrical connection without hindering the covering of the first support shell 11 and the second support shell 21 by the elastic covering unit 22 is within the protection scope of the invention.

By means of setting the membrane pressure-sensing units 12 on the first outer surface S01 of the first support shell 11 and the second outer surface S11 of the second support shell 21, the testing area and range can be enlarged and more information can be obtained.

Figure 6:
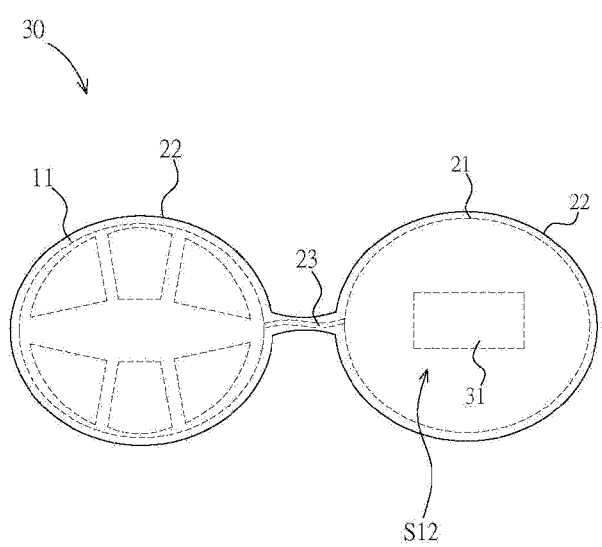
FIG. 6 is a schematic diagram showing the configuration of a muscle training apparatus according to the third embodiment of the invention.

The following embodiments are illustrated based on FIGS. 2 and 4 in addition to the corresponding diagrams. Please also refer to FIG. 6 to illustrate the muscle training apparatus of the third embodiment in the invention. As shown in FIG. 6, the difference between the muscle training apparatus 30 and the muscle training apparatus 20 of the abovementioned second embodiment is that the second outer surface of the second support shell 21 of the muscle training apparatus 30 is not provided with the membrane pressure-sensing units, but the muscle training apparatus 30 includes a force-generating unit 31.

Figure 7:
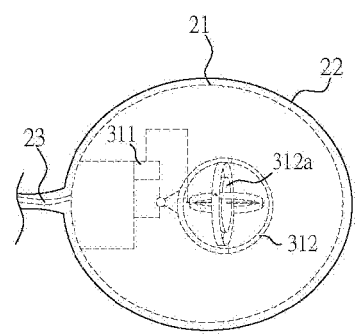
FIG. 7 is a schematic diagram showing the force-generating unit arranged in the second support shell of the third embodiment.

The force-generating unit 31 is arranged in the second containing space S12 of the second support shell 21 to generate a force in a specific direction. Also referring to FIG. 7, the force-generating unit 31 may include a motor 311 and a gyroscope 312. The former is electrically connected with the power supply unit 18 to receive the corresponding driving power, so as to drive a rotor 312*a* of the gyroscope 312 to rotate and generate the force corresponding to the earth gravity.

Figure 8:
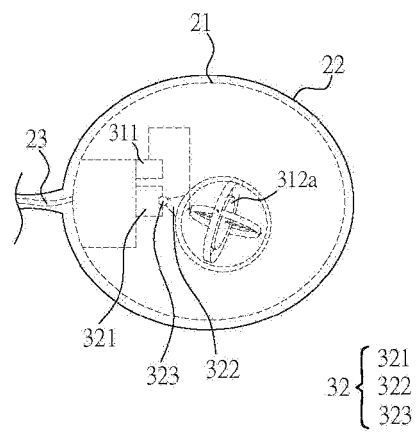
FIG. 8 is a schematic diagram showing the operation of the steering mechanism of FIG. 7.

Then, referring to FIG. 8, the muscle training apparatus 30 also includes a steering mechanism 32, which is connected to the gyroscope 312 to change the tilt angle of the gyroscope so as to change the magnitude and/or direction of the force. The steering mechanism 32 has a first fixing part 321, a second fixing part 322 and a pivot 323. The first fixing part 321 is fixed to the second support shell 21, the second fixing part 322 is fixed to the gyroscope 312, and the pivot 323 is connected between the first fixing part 321 and the second fixing part 322. Through driving the pivot 323, relative position between the gyroscope 312 and the second support shell 21 can be changed. In other embodiments, the pivot 323 can be uniaxial or multiaxial, or even 360-degree universal rotation, which is not limited here.

And in other embodiments, the muscle training apparatus 30 may include a control unit (not shown in the figure), which is electrically connected to motor 311 and the arithmetic processing unit 14, respectively. The control unit can control the speed of the motor by converting the information output by the arithmetic processing unit 14 into a control signal. Besides, the control unit can be electrically connected with a driving unit of the pivot 323 to control the steering angle of the pivot 323.

In other embodiments, the muscle training apparatus may include a plurality of force-generating units, which can be set in the support shell at different angles to generate forces in different directions and intensities, thereby adjusting the muscle training mode.

Moreover, in other embodiments, the power supply unit 18, the arithmetic processing unit 14, the storage unit 16, the signal transmission unit 17 and the control unit can be selectively arranged in the first containing space S02 of the first support shell 11, or the second containing space S12 of the second support shell 21, which is not limited here.

What is more, the first support shell 11 with the membrane pressure sensing units 12 and the second support shell 21 with the force-generating unit 31 can be separated and used as individual component.

In summary, the muscle training apparatus of the invention uses a plurality of membrane pressure sensing units arranged on the first support shell and/or the second support shell for muscle strength detection. The omni-directional muscle pressure can be obtained through the membrane pressure sensing units distributed on the outer surface of the first support shell and/or the second support shell, and then be converted to the corresponding muscle state by the arithmetic processing unit, so that the muscle strength can be known by users or doctors. In addition, the force-generating unit can generate forces in specific direction and intensity to achieve the effect of training on specific muscle groups.

Even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

What is claimed is:

1. A muscle training apparatus capable of generating a force, comprising:
   a second support shell, which is spherical and has a second containing space;
   a force-generating unit, which is arranged and fixed in the second containing space to generate a force;
   a steering mechanism, which is arranged in the second containing space and is connected between the force-generating unit and the second support shell, and moving the force-generating unit relative to the second support shell to change the magnitude and/or direction of the force; and an elastic covering unit, which covers the second support shell.

2. The muscle training apparatus of claim 1, wherein the elastic covering unit is an integrally formed silica gel.

3. The muscle training apparatus of claim 1, wherein the force-generating unit comprising:
- a gyroscope, which has a rotor and generates force through the rotation of the rotor; and
- a motor, which is connected with the rotor of the gyroscope to drive the rotor.

4. The muscle training apparatus of claim 3, wherein the steering mechanism is connected between the gyroscope and the second support shell to move the gyroscope relative to the second support shell.

5. The muscle training apparatus of claim 1, wherein the steering mechanism comprising:
- a first fixing part, which is connected to the second support shell;
- a second fixing part, which is connected to the force-generating unit; and
- a pivot, which is connected between the first fixing part and the second fixing part, wherein the force-generating unit is moving relative to the second support shell.

6. The muscle training apparatus of claim 1, further comprising:
- a power supply unit, which is arranged in the second containing space of the second support shell to output a power supply.

7. A muscle training apparatus capable of generating a force, comprising:
- a second support shell, which is spherical and has a second containing space;
- a force-generating unit, which is arranged and fixed in the second containing space to generate a force;
- an elastic covering unit, which covers the second support shell;
- a first support shell, which is spherical and has a first outer surface and a first containing space;
- a plurality of membrane pressure sensing units, which are respectively arranged on the first outer surface of the first support shell;
- an arithmetic processing unit, which is arranged in the first containing space of the first support shell and is electrically connected with the membrane pressure sensing units; and
- a signal transmission unit, which is arranged in the first containing space of the first support shell and is electrically connected with the arithmetic processing unit.

8. The muscle training apparatus of claim 7, further comprising:
- a power supply unit, which is arranged in the first containing space of the first support shell to output a power supply.

9. The muscle training apparatus of claim 7, wherein the first support shell has a first end and a second end, which are arranged opposite to each other, the first end is divided into four quadrants according to an axis, each quadrant is provided with at least one membrane pressure sensing unit.

10. The muscle training apparatus of claim 7, wherein the signal transmission unit is a wireless signal transmission unit.

11. The muscle training apparatus of claim 7, wherein the elastic covering unit further covers the first support shell.

* * * * *